United States Patent [19]
Bartman et al.

[11] Patent Number: 5,415,025
[45] Date of Patent: May 16, 1995

[54] MASS SPECTROMETER-BASED CONTINUOUS EMISSIONS MONITORING SYSTEM FOR HAZARDOUS WASTE STACK GAS MEASUREMENTS

[75] Inventors: Candace D. Bartman, Gilbert, S.C.; James H. Renfroe, Jr., Morgan City, La.; Henry L. Robards, Jr., Thibodaux, La.; Erin M. Connolly, Morgan City, La.

[73] Assignee: Marine Shale Processors, Inc., Saint Rose, La.

[21] Appl. No.: 217,763

[22] Filed: Mar. 25, 1994

Related U.S. Application Data

[63] Continuation of Ser. No. 984,271, Dec. 1, 1992, abandoned, which is a continuation of Ser. No. 601,299, Oct. 22, 1990, abandoned.

[51] Int. Cl.[6] ............... G01N 1/22; G01N 31/00
[52] U.S. Cl. ............... 73/23.2; 73/863.11; 73/863.23; 73/864.81
[58] Field of Search ............... 73/23.2, 863.23, 864.81, 73/31.05, 863.24, 863.81, 863.11, 1 G

[56] References Cited

U.S. PATENT DOCUMENTS

| | | | |
|---|---|---|---|
| 3,718,434 | 2/1973 | Pierce | 73/31.07 |
| 3,848,548 | 11/1974 | Bolejack, Jr. et al. | 110/7 R |
| 3,960,500 | 6/1976 | Ross et al. | 73/863.11 |
| 4,073,619 | 2/1978 | Lawson | 73/863.11 |
| 4,094,187 | 6/1978 | Navarre, Jr. | 73/1 G |
| 4,578,986 | 4/1986 | Navarre | 73/1 G |
| 4,856,352 | 8/1989 | Daum et al. | 73/1 G |
| 4,974,453 | 12/1990 | Hohorst | 73/863.11 |
| 4,974,455 | 12/1990 | McGowan et al. | 73/863.12 |

FOREIGN PATENT DOCUMENTS

| | | | |
|---|---|---|---|
| 1094955 | 9/1986 | European Pat. Off. | G01N 1/24 |
| 8421369.8 | 9/1987 | Germany | G01N 1/24 |
| 1496887 | 1/1978 | United Kingdom . | |

OTHER PUBLICATIONS

Nelson, J.; (1987) "Continuous Measurement of HCl Emissions from MSW Incineration Facilities," Proceedings, Air Pollution Control Association International Speciality Conference On The Thermal Treatment of Municipal, Industrial and Hospital Waste, Pittsburgh, Pa., p. 183.

Buonicore, "Experience with Air Pollution Control Equipment . . . " Journal of Hazardous Materials, 22(1989) pp. 232–242.

Whitehurst et al., "Design of a Real-Time Stack Monitoring . . . " presented at the International Incinerator Conference, Knoxville, Tenn. May 4 '89.

The Daily Review, Continuous Monitoring System Brings MSP Worldwide Acclaim, vol. 27, No. 115, Jun. 9, 1989.

C. A. Whitehurst et al., Monitoring Emissions For A Hazardous Waste. Presented to the 5th International Conference on Hazardous Waste Management, Technology and Public Policy, Rome, Italy, Apr. 1989.

(List continued on next page.)

*Primary Examiner*—Hezron E. Williams
*Assistant Examiner*—Michael J. Brock
*Attorney, Agent, or Firm*—Finnegan, Henderson, Farabow, Garrett & Dunner

[57] ABSTRACT

Disclosed is a continuous emissions monitoring system for exhaust gas emissions containing HCl comprising a sampling subsystem with a sample probe in the effluent to collect effluent samples that are transmitted through heated conduits through one or more filters and pumps to a mass spectrometer. The sampling subsystem is maintained at a temperature no less than about 190° C. and the flow rate through the system is greater than about 10 liters per minute. The process for continuous monitoring of exhaust emissions containing HCl extracts an exhaust gas sample and maintains the temperature and physical state of the exhaust gas throughout transport of the sample from the exhaust effluent to a mass spectrometer.

10 Claims, 7 Drawing Sheets

OTHER PUBLICATIONS

George Harlow, et al., Design of a Continous Emissions Monitoring System at a Manufacturing Facility Recycling Hazardous Waste, Presented to Hazardous Materials Control Research Institute, Great Lakes 90, Sep. 1990.

Candace D. Bartman et al., A Mass Spectrometer-Based Continuous Emissions Monitoring System for Hazardous Waste Stack Gas Measurements. Presented at the International Joint Power Generation Conference and Exposition, Oct. 22, 1990.

E. Timothy Oppelt, Incineration of Hazardous Waste, The International Journal of Air Pollution Control and Waste Management (JAPCA), vol. 37, No. 5, May, 1987, 558–586.

Kun–chieh Lee, Research Areas for Improved Incineration System Performance, The International Journal of Air Pollution Control and Waste Management (JAPCA), vol. 38, No. 12, Dec. 1988, 1542–1550.

C. C. Lee, et al., Hazardous/Toxic Waste Incineration, Journal of the Air Pollution Control Assoc., vol. 36, No. 8, Aug. 1986, 922–931.

Edward B. Overton, Development of Real–Time Stack–Gas Analysis Methods, Journal of Hazardous Materials, 22 (1989) 187–194.

R. A. Bartera et al., "Continuous HCl Air Indicator", NASA Tech Briefs, vol. 1, No. 1, p. 69, 1976.

M. Ascherfeld et al., "Beheizbares Gasanalysensystem Zur Kontinuierlischen Extraktiven Messung", Technisches Messen TM, vol. 54, No. 5, pp. 195–199, 1987.

PCT International Search Report dated Mar. 4, 1992.

PCT International Preliminary Examination Report dated Sep. 18, 1992.

MASS SPECTROMETER-BASED CONTINUOUS EMISSIONS MONITORING SYSTEM FOR HAZARDOUS WASTE STACK GAS MEASUREMENTS

This application is a continuation of application Ser. No. 07/984,271, filed Dec. 1, 1992, now abandoned which is a continuation of application Ser. No. 07/601,299, filed Oct. 22, 1990, now abandoned.

BACKGROUND OF THE INVENTION

Over the past several years, the need for limiting stack gas emissions at industrial facilities which process hazardous waste has become a topic of increasing importance. Government regulations are now pending for boilers and industrial furnaces burning hazardous waste as fuels or for recycling and methodology for continuous emissions monitoring systems (CENS) is currently being evaluated.

Among the compounds for which emissions limits will be set are HCl, $SO_2$ and nitrogen oxides, $NO_x$. At the present time, only a limited number of CEMS for HCl are installed in industrial environments and, as noted by Buonicore in "Experience with Air Pollution Control Equipment and Continuous Monitoring Instrumentation on Hazardous Waste Incinerators," *Journal of Hazardous Materials*, 1989, Vol. 22, pp. 233–242, the reliability of these systems has yet to be proven.

In December of 1989, the USEPA requested comments on "whether continuous emissions monitoring for HCl would be a feasible, practical requirement in lieu of waste analysis for chlorine to limit HCl emissions." The ASME Research Committee on Industrial and Municipal Wastes responded that only one of five monitoring devices found by the EPA to be "acceptable" was actually reliable in plant operations. The Committee noted that service and support on the device, which is based on infrared technology and produced in West Germany, has been inadequate to date. The Committee therefore concluded that continuous monitoring for HCl may be appropriate at large facilities but is inappropriate at smaller facilities.

A number of parameters in stack gas emissions can be used to evaluate the totality of the combustion process and the adequacy of the emission control system. For example the amounts of $O_2$ $CO_2$, $SO_2$ and nitrogen oxides, $NO_x$, present can indicate if the thermal degradation process is complete. See Oppelt "Incineration of Hazardous Waste, A Critical Review," *Journal of Air Pollution Control and Waste Management*, 1987, Vol. 37, No. 5, pp. 558–586, and C. Lee et al., "An Overview of Hazardous/Toxic Waste Incineration," *Journal of Air Pollution Control and Waste Management*, 1986, Vol. 36, No. 5, pp. 922–931, for reviews of the usefulness of these gases as indicators and the CEMS technology currently available for their measurement.

Products of incomplete combustion (PICs) are also components in stack gas for which public concern is high due to their potential toxicity. As noted by K. Lee in "Research Areas for Improved Incineration System Performance," *Journal of Air Pollution Control and Waste Management*, 1989, Vol. 38, No. 12, pp. 1542–1550, their formation and emissions of PICS are not well understood. Continuous monitors are not yet commercially available although Overton, "Development of Real-Time Stack-gas Analysis Methods," *Journal of Hazardous Materials*, 1989, Vol. 22, pp. 187–194, recently reported on a microbore gas chromatographic method which appears promising.

Continuous data for $SO_2$ and HCl emissions can help insure that these gases are adequately neutralized by the scrubbing system. As noted by Podlenski in "Feasibility Study for Adapting Present Combustion Source Continuous Monitoring Systems to Hazardous Waste Incinerators," *EPA Report No.* 600/8-84-011a, 1984, such data can provide information that can be used as a guide for design and operation purposes. At the present time, however, the EPA accepted technology for HCl monitoring is a manual sampling method with subsequent laboratory analysis by either titration or ion chromatography.

In order to improve performance at industrial facilities processing hazardous waste and to monitor stack gas emissions for the purpose of risk assessment, there has been a longstanding need for a CEMS which efficiently monitors exhaust gases, especially HCl.

A CEMS consists of two major subsystems, an analytical subsystem and a sample extraction subsystem, each of which must be considered in the development of a complete system for continuous stack gas measurement. A variety of analytical technologies including gas chromatography, fourier transform infrared spectroscopy, photoacoustic spectroscopy, ion mobility spectrometry and mass spectrometry were evaluated and a commercially available mass spectrometer was chosen as the analytical subsystem. The advantages and disadvantages of the technologies mentioned above for this intended purpose has been discussed by Harlow et al., "Design of a Continuous Emissions Monitoring System at a Manufacturing Facility Recycling Hazardous Waste," *Proceedings, Hazardous Materials Control Research Institute, Great Lakes* 90, Cleveland, Oh., pp. 285–289, 1990.

As noted previously, use of CEMS to monitor compounds such as $O_2$ and nitrogen oxides, $NO_x$ is known. These compounds can be delivered to an analytical instrument while allowing the stack gas to cool since they are gases at routine ambient temperatures. In addition, none of these substances are very reactive, making sample extraction systems for these compounds relatively straight forward. There is no need for a heated system and most particulate material is removed with the water. However, conventional CEMS sample extraction is unsatisfactory for compounds such as HCl.

SUMMARY OF THE INVENTION

The objective of this invention is to provide a mass spectrometer-based continuous emissions monitor with a heated sample extraction system. A further object of the present invention is to provide CEMS capable of continuous measurement of at least $O_2$, $CO_2$, $SO_2$, $NO_x$, and HCl. Another object of the present invention is to develop a heated sample extraction subsystem that would keep HCl in the vapor phase, prevent corrosion and minimize problems associated with the reactive nature of HCl.

One embodiment of the present invention is a process for continuously monitoring the gaseous exhaust of an effluent stream containing HCl. The process comprises the steps of: extracting a sample of a gaseous effluent from an effluent stream; transporting the sample at the desired sample. temperature; hot filtering the sample; transferring the filtered sample through a heated transfer line to a heated analyzing station; maintaining a flow rate of the filtered sample of at least 10 liters per minute;

and analyzing the filtered sample by mass spectrometry. Throughout the entire process the sample is maintained at a temperature no less than about 190° C.

Another embodiment of the present invention is a system for providing compositionally representative samples of the gaseous component of an effluent stream consisting of a mixture of gas, vapor and particulate material. The system comprises a sampling means within the effluent stream for continuously extracting samples of that stream; a conduit in flow communication with the sampling means, the conduit is heated by the effluent stream; a heated filtering system in flow communication with the conduit, the filtering system removes particulates from the samples; at least one heated transfer line in flow communication with the heated filtering system; an analyzer in flow communication with the transfer line, the analyzer comprises a heated sample pump and a heated capillary stem for sample introduction into a mass spectrometer, the pump is located in close proximity and upstream from the capillary stem and maintains a flow rate of at least 10 liters per minute within the sampling system. The sampling system, conduit, heated filtering system, heated transfer line and the sample pump are maintained at a temperature of not less than about 190° C.

A third embodiment of this invention is a continuous emissions monitoring system comprising the heated sampling system described above and a mass spectrometer.

BRIEF DESCRIPTION OF DRAWINGS

FIG. 3 is a detail drawing of (a) the probe connection in the sample extraction subsystem and (b) of a standard gas connection in the sample extraction system used for calibration.

DESCRIPTION OF THE PREFERRED EMBODIMENTS

The mass spectrometer biased continuous emissions monitoring system (CEMS) has two subsystems, the sample extraction subsystem and the mass spectrometer subsystem. The mass spectrometer subsystem, which measures the percent concentration of individual components of the stack gas sample, consists of the mass spectrometer hardware and the data acquisition equipment. The sample extraction subsystem's function is to deliver the stack gas sample to the mass spectrometer without changing the state or composition of the gaseous and vapor portions of the extracted sample.

Sample Extraction Subsystem

The design criteria for the sample extraction subsystem included:
1) heating of the system in its entirety to avoid water condensation with subsequent loss of HCl;
2) adequate filtration to remove particulate material larger than one micron;
3) a pumping system with sufficient capacity to draw the sample from the stack with minimum delay time; and
4) ease of maintenance.

Figure 1:
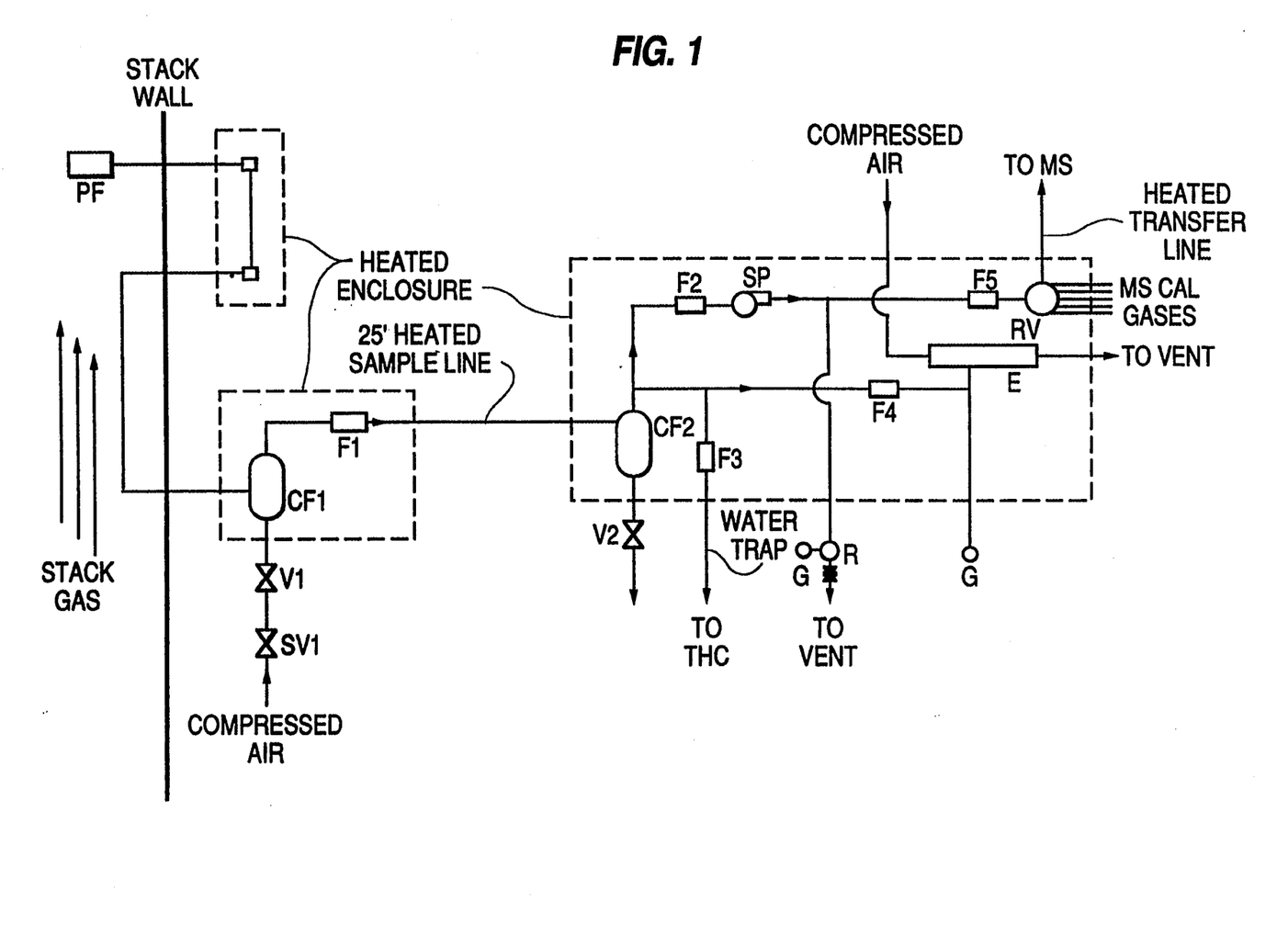
FIG. 1 is a schematic drawing of the sample extraction subsystem according to a preferred embodiment of the invention.
Figure 3A:
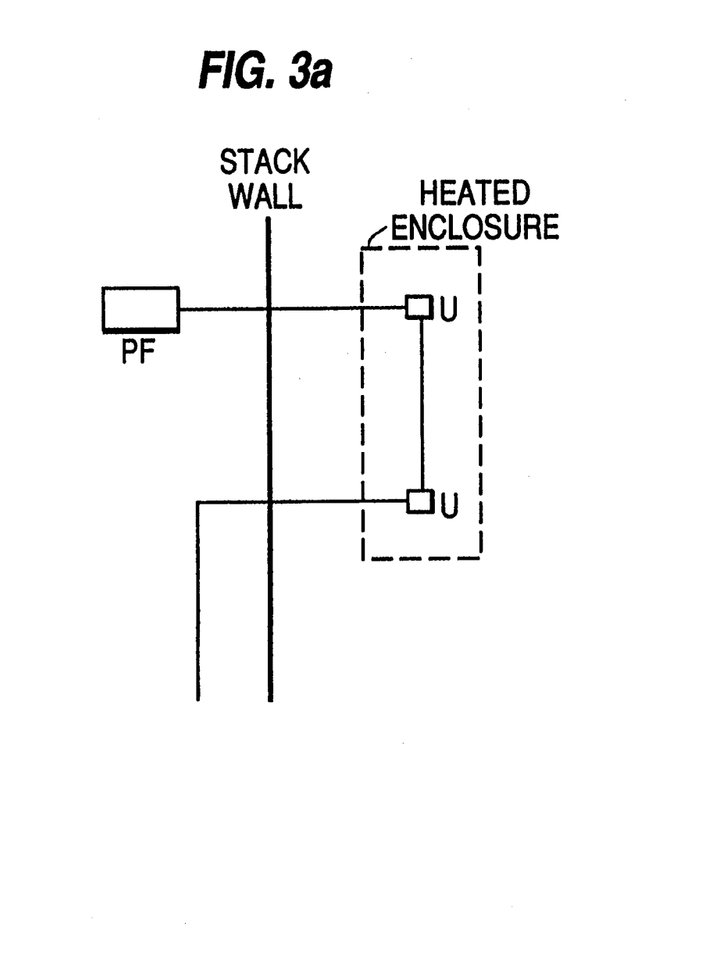
Figure 3B:
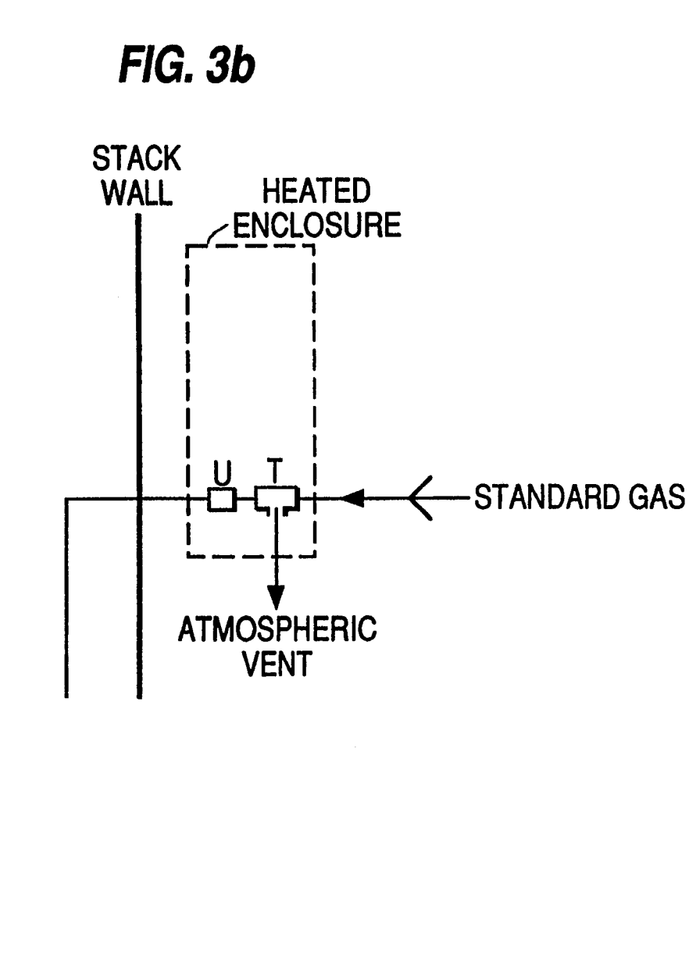

FIG. 1 shows a schematic of the preferred sample extraction system of this invention. The following symbols are used in FIGS. 1 and 3:

| | |
|---|---|
| CF1, CF2 | cyclone filters |
| V1, V2 | manual valves |
| F1–F5 | filters |
| PF | probe filter |
| SV1 | solenoid valve |
| RV | rotary valve |
| E | eductor |
| R | back pressure regulator |
| THC | total hydrocarbon analyzer |
| U | union |
| T | tee. |

A sampling means, preferably a sample probe consisting of a 30 micron filter mounted on a stainless LAW steel tube, is installed inside the exhaust stack approximately 8 stack diameters downstream from the input conduits of the fans driving the effluent through the exhaust stack, and 8 stack diameters upstream from the effluent exhaust at the end of the stack. A sample line then runs through the exhaust stack and within the effluent to allow the heat of the exhaust stack to maintain the desired sample temperature, thus eliminating the need for a long transfer line that must be heated and maintained. The sample line may first run from the sampling means to a heated maintenance enclosure mounted on the exhaust stack wall which facilitates maintenance of the probe and provides a point for connection of standard gases used in calibration and testing.

At the base of the stack the exhaust sample line enters a second heated enclosure which houses a series of filters comprising a first filter, preferably a cyclone filter, to remove large particulates and a secondary filter, preferably a ceramic glass microfiber filter, to remove small particulates. Small particulates are those having sizes less than about 5 microns to about 0.1 micron. A source of compressed air may be connected to the first filter to blowback the system periodically to avoid sample line and filter blockage. The exhaust gas sample then passes through a heated transfer line to a heated analyzing station.

The heated analyzing station comprises a pump, preferably an eductor, is used to move at least 10 liters per minute, preferably about 15 liters per minute, of the exhaust gas sample from the stack to the enclosure upstream from mass spectrometer, and a heated capillary for sample introduction into the mass spectrometer. The analyzing station may also contain a second series of filters to further remove particulate material. Preferably the second series of filters comprises a cyclone filter to remove large particulates and a second ceramic filter to remove small particulates. Only particles smaller than 0.1 micron pass the final filter. After filtration, the exhaust gas sample may be split and directed to a total hydrocarbon analyzer. A second pump, preferably a diaphragm pump equipped with a backpressure regulator at the outlet side of the pump, insures that an appropriate flow of sample is delivered to the mass spectrometer. The filtered exhaust gas sample may be connected to the mass spectrometer via computer-controlled 16 position rotary valve which may also have connections to mass spectrometer calibration gases.

To accurately analyze for HCl it is critical to maintain the sample at the appropriate elevated temperature. The slightest cold spot that allows condensation of water not only removes HCl but causes particulate to drop out of the gas stream with subsequent blockage. For analysis of HCl, the system is heated to a temperature no less than about 190° C. In addition, HCl is an extremely reactive substance which can lead to corrosion. The elevated temperatures, which insure that HCl remains in the vapor phase, eliminates corrosion problems.

The reactive nature of HCl can lead to "wall affects", the adsorption to and desorption from surfaces. Construction materials are therefore an important consideration in minimizing these affects. Preferably materials such as teflon and stainless material are used as they show the least propensity to adsorb HCl.

The following changes are preferably made to the mass spectrometer to reduce HCl adsorption and improve response. First, the rotary valve rotor and a mass spectrometer ferrule, ordinarily made of a graphite and vespel composite, are replaced with components made of teflon. Next, the mass spectrometer's ionizer, which has a large surface area, is replaced with an "open" ionizer constructed of wire mesh in an effort to reduce the surface area available in the mass spectrometer to adsorb/desorb HCl.

Figure 2:
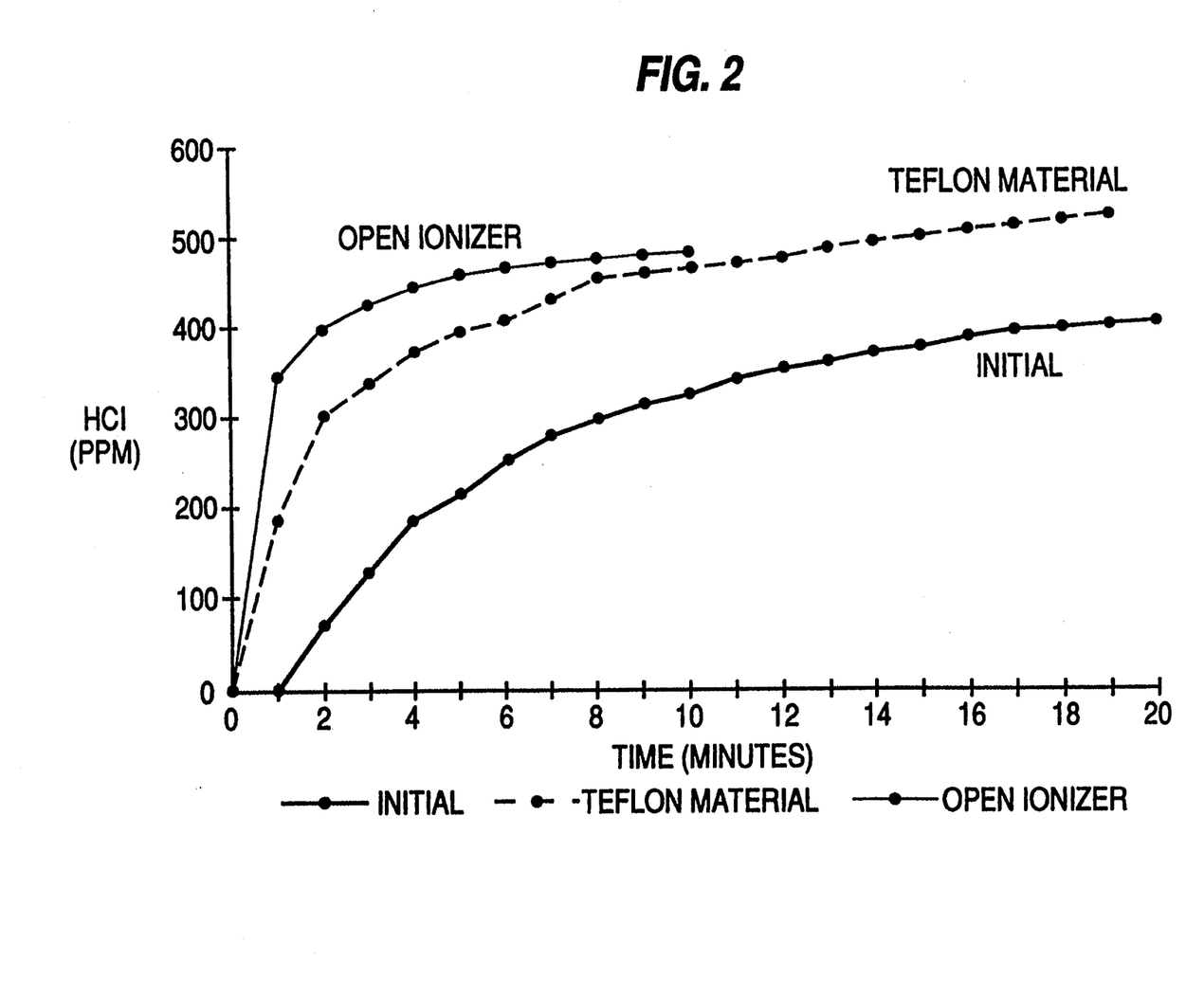
FIG. 2 shows the improvement in HCl response of the mass spectrometer after the above modifications.

FIG. 2 shows the improvement in HCl response of the mass spectrometer after the above modifications. The lower curve labelled "Initial" is the response prior to modification. The middle curve labelled "Teflon" shows the improvement with a change of material. The upper curve labelled "Open Ionizer" shows the improved response with the open screen-type ionizer.

Sample flow rate also appears to have a dramatic effect on the adsorption of HCl. It had been reported by Nelson that HCl has a tendency to adsorb on material surfaces at flow rates less than 10 liters per minute. See Nelson, "Continuous Measurement of HCl Emissions from MSW Incineration Facilities," *Proceedings, Air Pollution Control Association International Speciality Conference on the Thermal Treatment of Municipal, Industrial and Hospital Waste*, Pittsburgh, Pa.., p. 183 (1987).

Although the flow from the sample source in the exhaust stack to the outlet of the diaphragm pump was 15 liters per minute, the flow dropped dramatically at the rotary valve. Therefore, the fused silica capillary inlet of the mass spectrometer was moved from the common outlet of the rotary valve to the outlet of the diaphragm pump where flow rates are high. In the present invention flow rates greater than about 10 liters per minute, preferably about 15 liters per minute, which show a lower tendency for adsorption, are employed.

Relative accuracy tests for HCl were repeated with the modified instrument and inlet configuration. The data in Table 6 show that the relative accuracy for HCl obtained with the new configuration was 5.8%, well within the EPA requirement and more in line with the accuracies obtained for the other gases tested.

Mass Spectrometer Subsystem

The mass spectrometer used in the invention is a process mass spectrometer which continuously introduces the gas stream directly into the analyzer and monitors specific ion intensities for each component in the stream. A preferable mass spectrometer is a Questor Process Analyzer manufactured by Extel Corporation of Pittsburgh, Pa.

When the sample enters the mass spectrometer's vacuum chamber, it flows through a region referred to as an electron impact ion volume. Some percentage of the sample molecules collide with electrons thereby producing positively charged molecular ions and fragment ions. The ions thus formed are electrically removed from the ion region using a series of lenses and are "shot" into the quadrupole mass filter which separates the ions according to their mass-to-charge ratio. A mass spectrum, a plot of ion intensity versus mass-to-charge ratio, for every component is unique. In process mass spectrometry, a single ion is chosen for each component to be analyzed. In situations where the ion intensity is the result of several components in the stream, the component of interest is resolved mathematically by subtraction of the interfering components' ion intensities.

The components to be monitored are easily selected using the mass spectrometer's data system to create an "analysis method". In the present invention, the instrument is preferably set to continuously monitor $SO_2$, nitrogen oxides (as NO), HCl, $Cl_2$, $N_2$, $O_2$, $CO_2$ and Ar. An analysis of the eight components is completed every three seconds with the data reported locally and sent to the plant control computer. The instrument automatically calibrates itself using certified standard blends which are connected to the rotary valve. The calibration routine takes approximately ten minutes to complete.

Reliability

Maintenance on the CEMS of the present invention is minimal. The mass spectrometer requires only routine cleaning and maintenance. The sample extraction system show no signs of corrosion during the period in which it was developed and tested and requires minimal maintenance consisting of daily blowback and periodic changes of the system filters. Filter changes are required two to three times monthly and take approximately one hour.

The following examples are intended to illustrate, not limit, the present invention.

EXAMPLES

These examples compare and contrast the present invention with and without the modifications described above for HCl analysis. Example 1 was conducted without those modifications. Example 2 presents results obtained with the modified system.

The calibration drift, calibration error and relative accuracy (RA) test methods used in these examples are outlined by the Environmental Protection Agency in 40 CFR (Part 60, Appendix B, Specifications 3 and 4) and an EPA draft performance specification for HCl. These methods are summarized briefly below.

Sample Introduction

Standard gases are introduced in two ways. First, for direct mass spectrometer introduction, cylinders were connected to the rotary valve (see FIG. 1) to introduce gas directly to the mass spectrometer. Introduction at this point bypasses all portions of the extraction system used for sample acquisition and conditioning and demonstrates the mass spectrometer's capabilities. Second, for introduction through the sample extraction system, standard gas cylinders are introduced at the maintenance enclosure for the probe. FIG. 3a shows the normal probe connection at the stack. For the tests conducted to assess sample system performance, the probe filter was disconnected and a tee inserted in its place (FIG. 3b). A standard gas cylinder was connected to one side of the tee and the cylinder pressure adjusted until there was gas flowing out of the tee at atmospheric pressure. This insured adequate sample for the sample extraction system without pressurizing the system.

Calibration Drift Test

The calibration drift test measures the stability of the CEMS calibration over time. The test is performed on both zero and high level standards. After instrument calibration, standards are introduced through the sample extraction system and a zero time measurement taken. After 24 hours, during which no maintenance, repair or adjustment took place, the standards are again introduced and a second measurement taken, the 24-hour reading. After the 24-hour measurement, the instrument is calibrated and the next 0-time measurement taken. The test is generally repeated for seven consecutive days.

For each 24-hour period, the calibration drift is calculated by the equation:

$$\text{Calibration drift} = \frac{\bar{d}}{\text{span value}} \times 100$$

where d=(0-time measurement)−(24-hour measurement)
span value=the upper limit of the CEMS measurement range specified for the facility.

Calibration Error Test

The calibration error test is designed to assess the accuracy and linearity of the CEMS over the entire measurement range. After instrument calibration on a concentration equal to the span value, zero, mid and high level standards are each introduced three times through the sample extraction system. The calibration error is calculated by the equation:

$$\text{Calibration error} = \left| \frac{\bar{d}}{\text{span value}} \right| \times 100$$

where $\bar{d}$=mean difference between the CEMS response and the known reference concentration.

Relative Accuracy

The relative accuracy test is used to validate the calibration technique and verify the ability of the CEMS to provide representative and accurate measurements. The CEMS measurement is compared to a reference measurement obtained using an EPA accepted Performance Test Method (PTM). A minimum of nine tests is generally performed for each compound evaluated. The relative accuracy is calculated by the equation:

$$\text{Relative Accuracy} = \frac{|\bar{d}| + |CC|}{\overline{PTM}} \times 100$$

where $|\bar{d}|$ =absolute value of the mean of the differences of the CEMS and PTM measurements
$|CC|$ =absolute value of the confidence coefficient
$= t_{0.976} \frac{S_d}{\sqrt{n}}$
$\overline{PTM}$=average reference measurement

EXAMPLE 1

In this example, only $O_2$, $CO_2$ and $SO_2$ were evaluated using a CEMS without the system modifications needed to ensure accurate HCl measurement as described above. As shown by the results below the system configuration used for these experiments was not adequate for accurately measuring HCl.

CEMS Configuration

Only $O_2$, $CO_2$ and $SO_2$ were evaluated since certified HCl standards were not available due to long delivery times from the gas manufacturer. Table 1 shows the comparison of the standard deviations (repeatability) obtained by introducing standards directly to the mass spectrometer and through the sample extraction system. The data compare well showing that the sample extraction system causes no degradation of the mass spectrometer response.

TABLE 1

| | | Repeatability | | | |
|---|---|---|---|---|---|
| | | Direct Introduction | | Through Sample | System |
| | % Conc. | Std. Dev. | % RSD | Std. Dev. | % RSD |
| $O_2$ | 8.438 | 0.009 | 0.11 | 0.012 | 0.15 |
| $CO_2$ | 5.259 | 0.009 | 0.16 | 0.008 | 0.15 |
| $SO_2$ | 0.102 | 0.002 | 0.26 | 0.001 | 0.23 |

$\% \text{RSD} = \frac{\text{STd. Dev.}}{\% \text{Conc.}} \times 100$

A calibration drift test was performed to measure the stability of the CEMS calibration over time. The results in Table 2 show that the average calibration drift for $O_2$, $CO_2$, and $SO_2$ for the seven measurements was at least a factor of ten better than the EPA requirement.

TABLE 2

| | Calibration Drift Tests | | |
|---|---|---|---|
| Compound | % Conc. Tested | Average MS Drift | EPA Requirement |
| $O_2$ | 0.00 | 0.02 | 0.5% from reference |
| $O_2$ | 18.11 | 0.04 | 0.5% from reference |
| $CO_2$ | 0.00 | 0.00 | 0.5% from reference |
| $CO_2$ | 11.21 | 0.05 | 0.5% from reference |
| $SO_2$ | 0.00 | 0.02 | 2.5% of span |
| $SO_2$ | 0.248 | 0.04 | 2.5% of span |

A calibration error test was conducted for $O_2$, $CO_2$, and $SO_2$ and HCl to assess the accuracy and linearity of the CEMS over the entire measurement range. The results in Table 3 show that the calibration errors for all components meet the EPA specification when calculated using the EPA formula. However, the calibration error for HCl is significantly higher than the errors for $O_2$, $CO_2$, and $SO_2$.

TABLE 3

| | Calibration Error Tests | | |
|---|---|---|---|
| Compound | % Conc. Tested | MS Error % Span | EPA Requirement |
| $O_2$ | 0.00 | 0.03 | Not required |
| $O_2$ | 8.40 | 0.11 | Not required |
| $O_2$ | 18.11 | 0.08 | Not required |
| $CO_2$ | 0.00 | 0.03 | Not required |
| $CO_2$ | 5.35 | 0.76 | Not required |

TABLE 3-continued

Calibration Error Tests

| Compound | % Conc. Tested | MS Error % Span | EPA Requirement |
|---|---|---|---|
| CO₂ | 11.21 | 0.13 | Not required |
| SO₂ | 0.00 | 0.22 | Not required |
| SO₂ | 0.103 | 0.00 | Not required |
| SO₂ | 0.248 | 0.44 | Not required |
| HCl | 0.00 | 3.3 | 5.0% of span |
| HCl | 0.0596 | 2.1 | 5.0% of span |
| HCl | 0.1560 | 2.1 | 5.0% of span |

Table 4a shows the mass spectrometer response for direct introduction of the mid level standards for HCl and $O_2$. In both cases, the errors are quite small, although it was noted that HCl took considerably more time to equilibrate to the certified value than $O_2$.

TABLE 4a

Calibration Error
Standards Introduced Directly to the MS

| Component | Certified Value | Measured Value | d | % Error |
|---|---|---|---|---|
| O₂ (% Conc.) | 8.40 | 8.44 | 0.04 | 0.48 |
| HCL | 596 | 593 | 3 | 0.50 |

Table 4b gives the data obtained during the calibration error test when standards were introduced through the sample extraction system.

TABLE 4b

Calibration Error
Standards Introduced through the Sample Extraction System

| Component | Certified Value | Measured Value | d | % Error | Change Made |
|---|---|---|---|---|---|
| O₂ (% Conc.) | 8.40 | 8.42 | 0.02 | 0.24 | Zero-Mid |
| O₂ | 8.40 | 8.44 | 0.04 | 0.48 | High-Mid |
| O₂ | 8.40 | 8.42 | 0.02 | 0.24 | Zero-Mid |
| HCl (ppm) | 596 | 475 | 121 | 20.3 | Zero-Mid |
| HCl | 596 | 679 | 83 | 13.9 | High-Mid |
| HCl | 596 | 509 | 87 | 14.6 | Zero-Mid |

The $O_2$ data compare well to that obtained with direct introduction. The HCl data is very poor by comparison and appears to be dependent upon the last gas analyzed. For example, when changing from the zero gas to the mid standard, the measured reading was low whereas the measured reading was high when changing from the high to mid standard.

Figure 4:
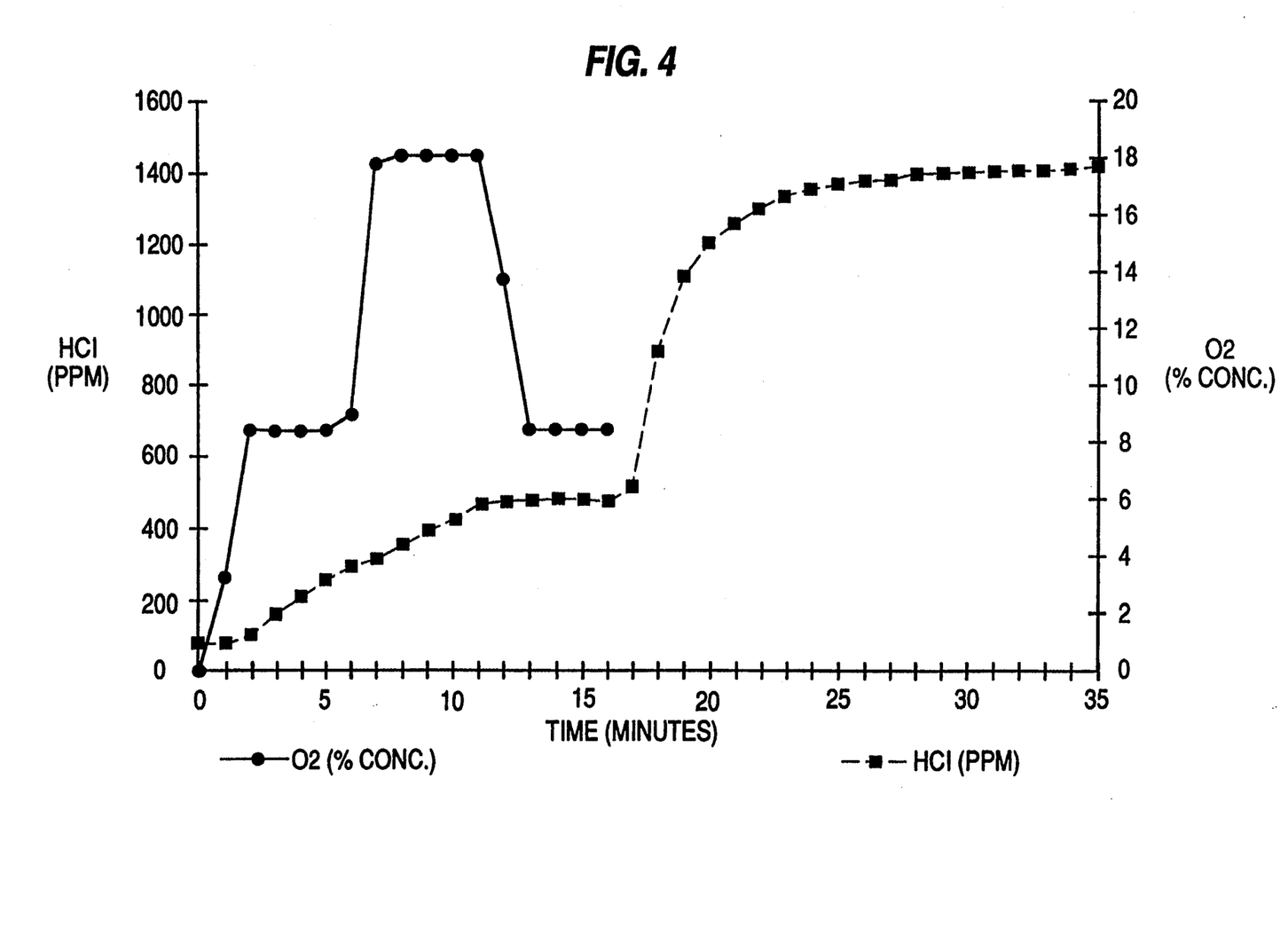
FIG. 4 is a plot of $O_2$ and HCl concentration versus time obtained while conducting the calibration error tests of Example 1.

A plot of $O_2$ and HCl concentration versus time obtained while conducting the calibration error tests is shown in FIG. 4 and further confirmed the system's sluggish response to HCl. The plot shows the mass spectrometer response when introducing the mid level and high level standards. Each data point is a one minute average of the mass spectrometer response. $O_2$ responded to the change in the gas standard within one minute and equilibrated to the certified concentration in less than three minutes whereas HCl had not equilibrated to the certified value after flowing the standard for 15 minutes.

Relative accuracy tests, designed to verify the ability of the CEMS to provide representative and accurate measurements, were conducted to further assess the CEMS' capability to analyze the gases of interest. The results in Table 5 show that $O_2$, $CO_2$, and $SO_2$ were well within the limits set by the EPA.

TABLE 5

Relative Accuracy Tests
Original CEMS Configuration

| Compound | MS % RA | EPA Requirement |
|---|---|---|
| O₂ | 3.8 | 20.0 |
| CO₂ | 2.5 | 20.0 |
| SO₂ | 5.8 | 20.0 |
| HCL | 22.1 | 20.0 |

EXAMPLE 2

The following tests were preformed with the modifications for HCl analysis described above.

Figure 5A:
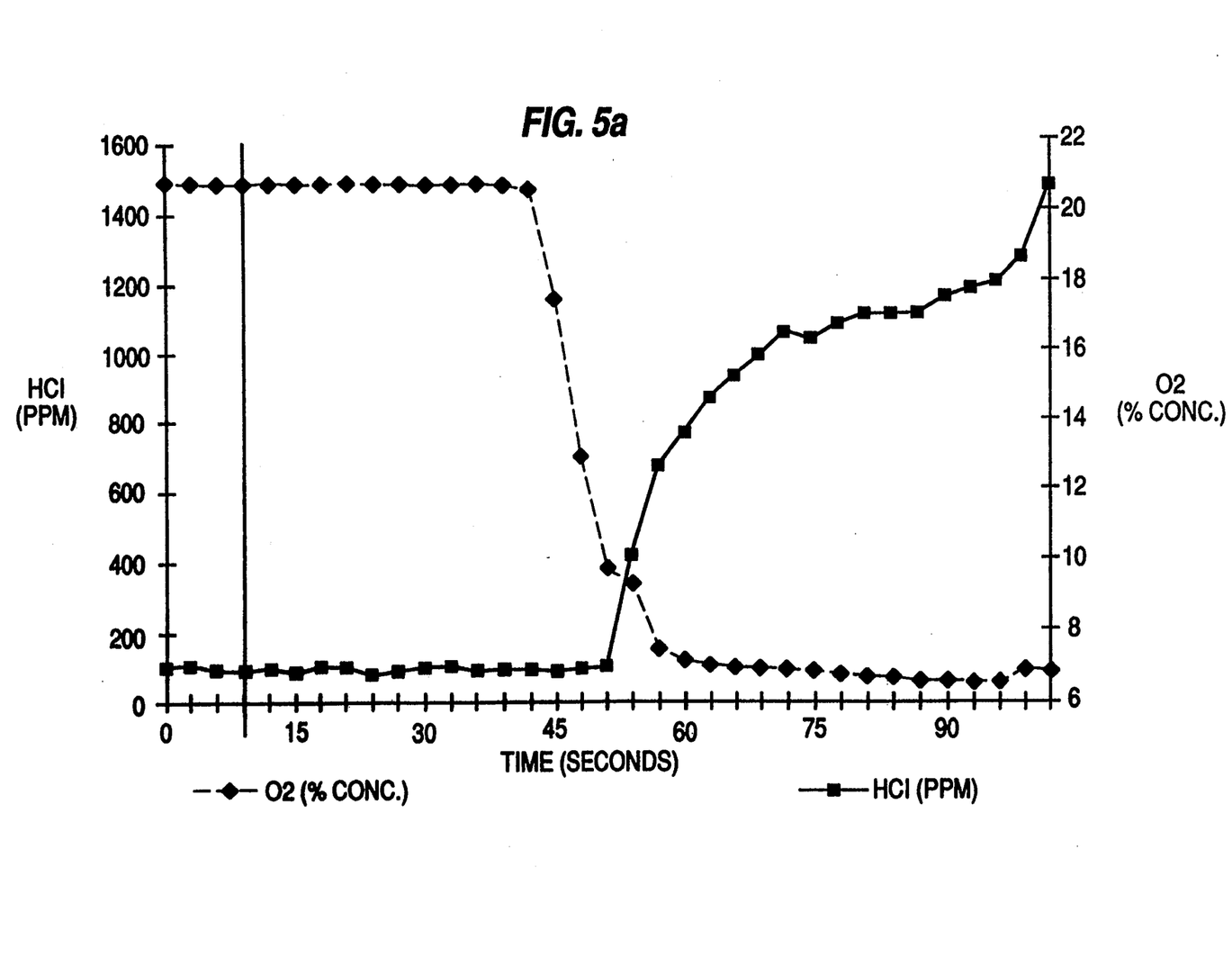
FIG. 5a shows the $O_2$ and HCl response curves when switching from blowback air to exhaust stack gas prior to modification for HCl analysis.
Figure 5B:
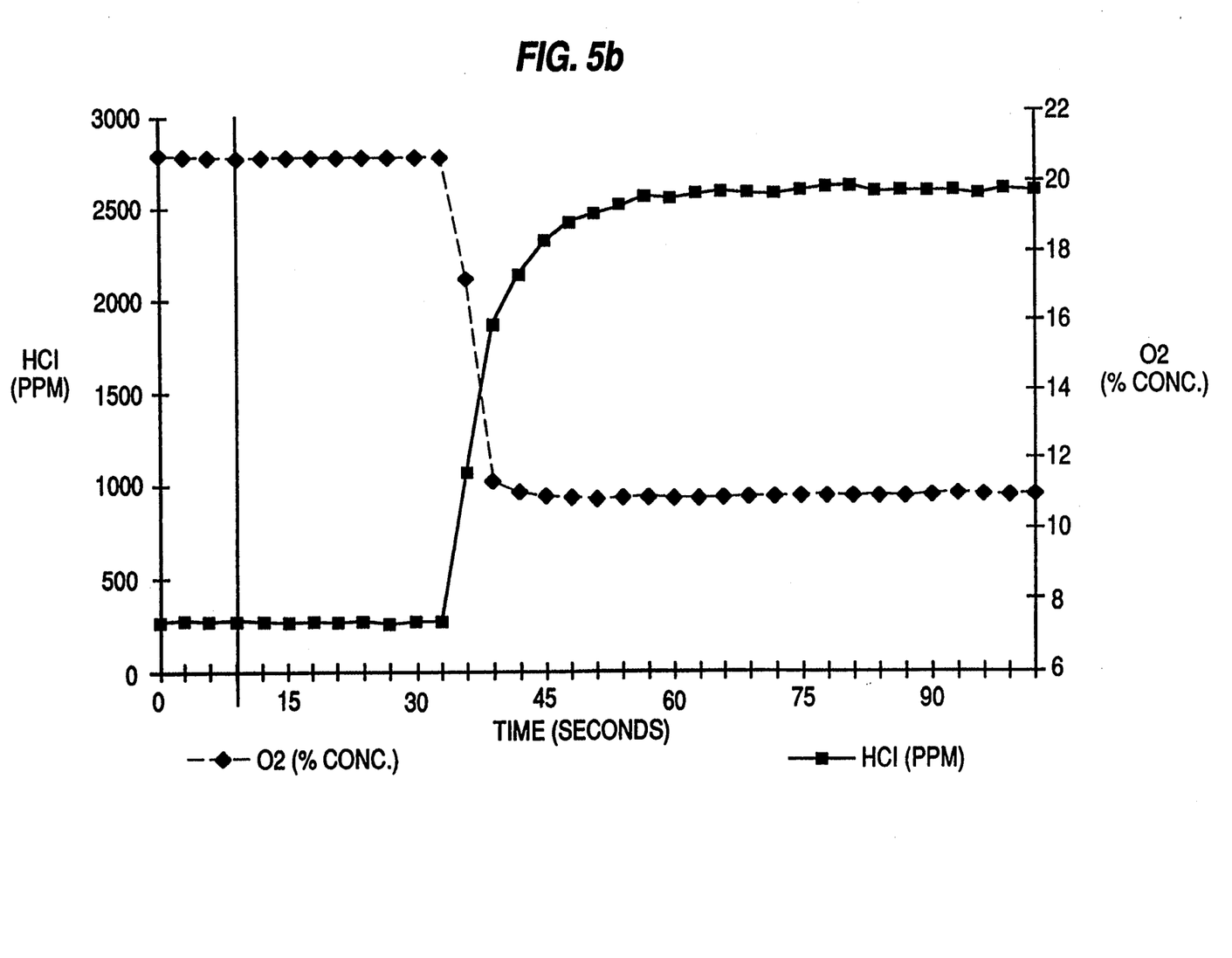
FIG. 5b shows the $O_2$ and HCl response curves when switching from blowback air to exhaust stack gas after modification for HCl analysis.

FIG. 5a shows the $O_2$ and HCl response curves when switching from blowback air to stack gas. The $O_2$ and HCl delay times were 36 and 45 seconds, respectively. $O_2$ equilibrated within approximately 75 seconds but HCl had not equilibrated by 93 seconds. FIG. 5b shows that with the modifications to the position of the fused silica capillary inlet described above the delay time for both $O_2$ and HCl was 27 seconds and that $O_2$ and HCl reached equilibrium within 39 and 54 seconds, respectively.

Relative accuracy tests for HCl were repeated with the modified instrument and inlet configuration. The data in Table 6 show that the relative accuracy for HCl obtained with the new configuration was 5.8%, well within the EPA requirement and more in line with the accuracies obtained for the other gases tested. There is, however, a wide variation in % error with two samples having an error as low as 0.4% to the highest error of 10.9%.

TABLE 6

HCl Relative Accuracy

| Run % | PTM (ppm) | MS (ppm) | d (ppm) | % Error |
|---|---|---|---|---|
| 1 | 546 | 525 | 21 | 3.8 |
| 2 | 650 | 712 | −62 | 9.5 |
| 3 | 721 | 800 | −79 | 10.9 |
| 4 | 731 | 671 | 60 | 8.2 |
| 5 | 845 | 821 | 24 | 2.8 |
| 6 | 921 | 1009 | 4 | 0.4 |
| 7 | 1101 | 1097 | 4 | 0.4 |
| 8 | 1377 | 1382 | −5 | 0.4 |
| 9 | 1385 | 1327 | 58 | 4.2 |
| % RA = 5.8% | | | | |

Figure 6:
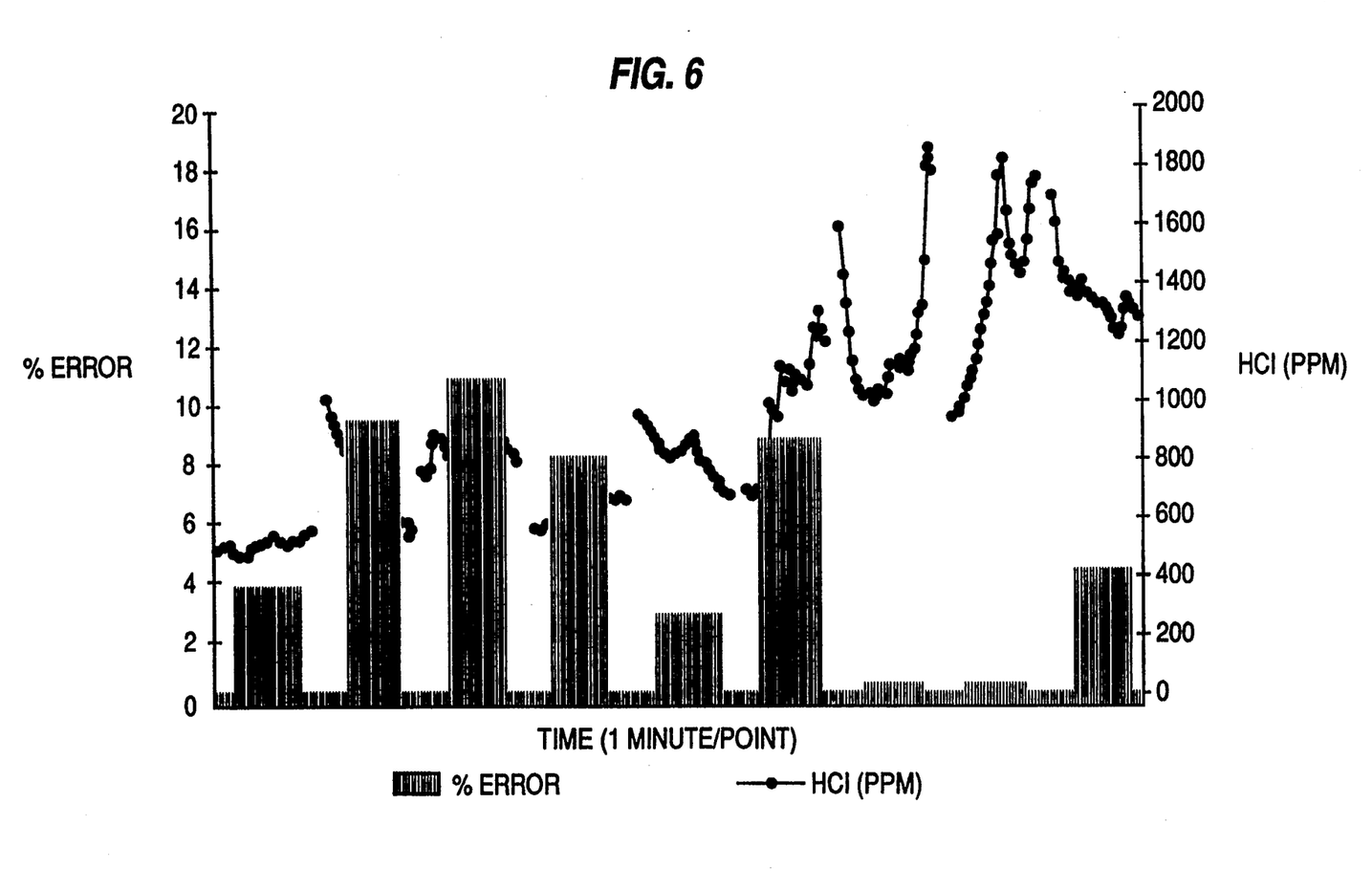
FIG. 6 is a plot of HCl gas concentration and percent error from the data obtained in the relative accuracy tests of the present invention in Example 2.

If the slower response time for HCl were related to higher % errors in the relative accuracy data, one would expect a high % error to occur when the concentration of HCl was rapidly changing during the sampling period and a low % error to be obtained when HCl concentration was relatively stable. FIG. 6 is a plot of HCl concentration during the periods of each relative accuracy test with a bar to indicate the % error obtained for that sample. There appears to be little correlation between the % error and concentration stability. Runs #7 and 8 had the lowest % error but were taken during a period when HCl concentration changed dramatically whereas Run #4, for example, shows a much more stable level of HCl but a much higher % error. During these relative accuracy tests, there was a significant problem with leaks at the ground glass joints of the impingers used to collect the stack gas for the performance test measurement which may have given rise to the variable % errors.

The results obtained in Examples 1 and 2 for the relative accuracy tests for $O_2$, $CO_2$, and $SO_2$ and HCl were well within the limits required by the EPA, indicating that a mass spectrometer with a carefully designed and implemented sample extraction appears to be viable alternative for continuous monitoring of stack gas emissions.

The present invention has been disclosed in terms of a preferred embodiment, however, the scope of the invention is not limited to this embodiment. The scope of the invention is determined solely by the appended claims and their equivalents.

What is claimed is:

1. A system for providing compositionally representative samples of the gaseous component of an effluent stream consisting of a mixture of gas, vapor and particulate material, said system comprising:

a sampler within said stream to continuously extract said samples therefrom;

an eductor in flow communication with said sampler, said eductor maintaining a flow rate of at least 10 liters per minute within said system between said sampler and said eductor;

a heated conduit in flow communication with said sampler;

a heated filter in said conduit, said filter disposed to remove particulates from said samples passing therethrough;

a heated transfer line in flow communication with said filter, for transferring said sample to a second and a third transfer line, said third transfer line being in flow communication with said eductor;

an analyzer subsystem in flow communication with said second transfer line, said analyzer subsystem comprised of a heated sample pump and a heated capillary for introducing said sample into a mass spectrometer, said pump being located in close proximity to and upstream from said capillary;

wherein said sampler, conduit, said heated filter, said heated transfer lines, and said pump being maintained at a temperature of not less than about 190° C.

2. The system of claim 1 wherein said educator maintains a flow rate of at least about 15 liters per minute.

3. The system of claim 1 wherein said sampler is comprised of a 30 micron filter mounted on a metal conduit.

4. The system of claim 1 wherein said system includes a computer controlled multiport valve in flow communication with said mass spectrometer, wherein said multiport valve is constructed of stainless steel and teflon.

5. The system of claim 1 wherein said filter comprises a microfiber filter.

6. The system of claim 1 wherein said system includes a heated enclosure between said sampler and said heated filter, said enclosure providing means for providing maintenance to said sampler.

7. The system of claim 6 wherein said heated enclosure between said sampler and said heated filter includes means for injecting gas into said system in a direction opposite to flow of samples through said system.

8. The system of claim 1 wherein said system includes a heated enclosure between said sampler and said heated filter, said enclosure including means for injecting calibration gases into said system proximate said sampler.

9. The system of claim 8 wherein said heated conduit runs within said effluent stream and generally parallel thereto and is primarily heated by said effluent stream.

10. The system of claim 1 wherein said heated conduit runs within said effluent stream and generally parallel thereto and is primarily heated by said effluent stream.

* * * * *

UNITED STATES PATENT AND TRADEMARK OFFICE
CERTIFICATE OF CORRECTION

PATENT NO. : 5,415,025
DATED : May 16, 1995
INVENTOR(S) : Candace D. Bartman et al.

It is certified that error appears in the above-indentified patent and that said Letters Patent is hereby corrected as shown below:

In the Abstract, front page, line 9, change "the-system" to --the system--.

In Claim 2, column 12, line 5, change "educator" to --eductor--.

Signed and Sealed this

Twenty-ninth Day of August, 1995

Attest:

BRUCE LEHMAN

Attesting Officer        Commissioner of Patents and Trademarks